United States Patent
Thomas et al.

(10) Patent No.: US 8,273,910 B2
(45) Date of Patent: Sep. 25, 2012

(54) PROCESS FOR SILYLATING MONOCARBOXYLIC ACIDS

(75) Inventors: Florian Thomas, Kallstadt (DE); Jochen Petzoldt, Weisenheim am Berg (DE); Martin Gärtner, Worms (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/636,960

(22) Filed: Dec. 14, 2009

(65) Prior Publication Data

US 2010/0152472 A1    Jun. 17, 2010

Related U.S. Application Data

(60) Provisional application No. 61/122,862, filed on Dec. 16, 2008.

(30) Foreign Application Priority Data

Dec. 16, 2008  (DE) .......................... 10 2008 054 740

(51) Int. Cl.
*C07F 7/04* (2006.01)
(52) U.S. Cl. ...................................... 556/442
(58) Field of Classification Search .................. None
See application file for complete search history.

(56) References Cited

U.S. PATENT DOCUMENTS

| | | | | |
|---|---|---|---|---|
| 4,593,055 A | * | 6/1986 | Gitlitz et al. | 523/122 |
| 2004/0073035 A1 | * | 4/2004 | Maase et al. | 546/187 |

FOREIGN PATENT DOCUMENTS

| | | |
|---|---|---|
| EP | 1 273 589 A1 | 1/2003 |
| EP | 1 431 301 A1 | 6/2004 |
| WO | WO 03/062171 A2 | 7/2003 |
| WO | WO 2005/061416 A1 | 7/2005 |

OTHER PUBLICATIONS

Abdel-Fattah Shihada et al., "Preparation and Spectroscopic Properties of $Me_3SiOP(S)Cl_2$, $Me_3SiOP(S)Br_2$, and $Me_3SiOP(O)Br_2$", Zeitschrift Für Naturforschung Teil B, vol. 35b, No. 8, Aug. 1980, pp. 976-980.

V. F. Mironov et al., "Silalactones and Silalactams", Chemistry of Heterocyclic Compounds, vol. 2, No. 2, Mar.-Apr. 1966, pp. 334-337.

V. I. Rakhlin et al., "Synthesis of Trimethylsilyl β-(2,2-Dimethylhydrazino)propionate", Russian Journal of Organic Chemistry, vol. 40, No. 1, 2004, pp. 127-128.

C. Palomo, "A Convenient Synthesis of Trimethylsilyl Carboxylates using N-Trimethylsilyl-2-oxazolidinone in the Absence of Catalysts", Synthesis, 1981, pp. 809-811.

Asoke Banerji et al., "A Short Synthesis of (+)-Mevalonolactone", Synthetic Communications, vol. 12, No. 3, 1982, pp. 225-230.

Yun-Fei Du et al., "A Study on the Heterogeneous Reaction of Trialkylsilyl Chlorides with Inorganic Salts and Monocarboxylates Catalysed by PEG400", Journal of Chemical Research, 2004, Issue 3, March, pp. 223-225.

* cited by examiner

*Primary Examiner* — Sudhakar Katakam

(74) *Attorney, Agent, or Firm* — Oblon, Spivak, McClelland, Maier & Neustadt, L.L.P.

(57) ABSTRACT

A process for preparing silylated monocarboxylic acids by reacting $C_2$-$C_{10}$-monocarboxylic acids with halosilanes of the general formula (I)

$$SiHal_{4-x}R_x \qquad (I)$$

in which
Hal is a halogen atom selected from the group of fluorine, chlorine, bromine and iodine,
R is independently hydrogen, $C_1$-$C_{10}$-alkyl or aryl and
x is an integer of 0 to 3
to form hydrogen halide in the presence of an auxiliary base, wherein the auxiliary base and the hydrogen halide form a salt which forms two immiscible phases with the product of value or the solution of the product of value in a suitable solvent and is removed.

18 Claims, No Drawings

PROCESS FOR SILYLATING MONOCARBOXYLIC ACIDS

The present invention relates to a process for preparing silylated monocarboxylic acids by converting monocarboxylic acids in the presence of an auxiliary base.

The silylation of carboxylic acids is known in the literature. For instance, A. Shihada et al. disclose, in Z. Naturforsch. B 1980, 35, 976-980, the reaction of acetic acid with trimethylchlorosilane in diethyl ether with addition of diethylamine. V. F. Mironov et al. describe, in Chem. Heterocycl. Compd. 1966, 2, 334-337, the silylation of substances including methacrylic acid, likewise with trimethylchlorosilane in the presence of N,N-diethylaniline as an auxiliary base in diethyl ether. A disadvantage of these processes is the formation of voluminous hydrochloride precipitates which are difficult to filter and lead to yield losses in the filtration. An economically attractive regeneration of the auxiliary base is made difficult by the complicated solids handling.

The silylation of acrylic acid with hexamethylsilazane is described by V. I. Rakhlin et al. in Russ. J. Org. Chem. 2004, 40 S. The reaction is disadvantageous since a continuous removal of the ammonia released is required. Moreover, the process requires long reaction times at elevated temperatures and affords only moderate yields.

The preparation of trimethylsilyl carboxylates is likewise described by C. Palermo in Synthesis 1981, 809-811, The carboxylic acid is reacted with N-trimethylsilyl-2-oxazolidone in halogenated solvents such as carbon tetrachloride or dichloromethane.

This reaction route is impracticable for industrial use, since, firstly, the use of a halogenated solvent is problematic. Furthermore, the synthesis is costly, since the preceding synthesis of the silylating reagent is additionally necessary. The 2-oxazolidone is removed from the product by costly and inconvenient crystallization and filtration.

The preceding synthesis of the silylating reagent is also disclosed in Synth. Commun. 1982, 12, 225-230 by Banerji et al. The reaction with the carboxylic acid gives rise to imidazole as a by-product, which has to be removed from the product by filtration with acceptance of yield losses.

Another preparation route is described by Y.-F. Du et al. in J. Chem. Res. Synop. 2004, 3, p. 223-225, This discloses the reaction of sodium acetate with trimethylchlorosilane in solvents such as diethyl ether, PEG-400 or benzene. The reactant used was the sodium salt of the carboxylic acid, which first had to be prepared and dried carefully. As a result, the synthesis gives rise to sodium chloride as a by-product, which has to be filtered off. WO 2003/062171 A2 discloses a process for removing acids which form as by-products in the course of the reaction or are added to the mixture, for example for pH regulation, from reaction mixtures by means of an auxiliary base such as 1-methylimidazole or 2-ethylpyridine. The acids form, with the auxiliary base, a liquid salt which is immiscible with the product of value and can therefore be removed by means of liquid-liquid phase separation. By way of example, silylations of alcohols or amines with halosilanes are described. Acids for removal which are disclosed are hydrochloric acid and acetic acid. A process for silylating monocarboxylic acids is not disclosed.

International application WO 2005/061416 A1 likewise discloses a process for removing acids from reaction mixtures by means of an auxiliary base, the auxiliary base being an alkylimidazole which has a solubility in 30% by weight sodium chloride solution at 25° C. of 10% by weight or less and whose hydrochloride has a melting point below 55° C. According to the teaching of this application, the auxiliary bases are used to remove acids which form in the course of the reaction or are added during the reaction, for example for pH regulation. A process for silylating monocarboxylic acids is not disclosed.

It was therefore an object of the present invention to provide a further, alternative process for silylating monocarboxylic acids, which is notable for high yields and high selectivity and is economically attractive.

The object is achieved by a process for preparing silylated monocarboxylic acids by reacting $C_2$-$C_{10}$-monocarboxylic acids with halosilanes of the general formula (I)

$$SiHal_{4-x}R_x \quad (I)$$

in which

Hal is a halogen atom selected from the group of fluorine, chlorine, bromine and iodine, R is independently hydrogen, $C_1$-$C_{10}$-alkyl or aryl and x is an integer of 0 to 3 to form hydrogen halide in the presence of an auxiliary base, wherein the auxiliary base and the hydrogen halide form a salt which forms two immiscible phases with the product of value or the solution of the product of value in a suitable solvent and is removed.

In the process according to the invention, silylated monocarboxylic acids are prepared in a simple and economically attractive manner, by virtue of the hydrogen halide released during the reaction and the auxiliary base forming a salt which is immiscible with the silylated monocarboxylic acid. The auxiliary base added surprisingly selectively removes the hydrogen halide and not the monocarboxylic acid from the reaction mixture. A simple phase separation can separate the product of value from this salt of the auxiliary base with the hydrogen halide. The silylation of the monocarboxylic acid proceeds rapidly and with high yields.

The process according to the invention is suitable for the reaction of $C_2$-$C_{10}$-monocarboxylic acids with halosilanes of the general formula (I). It is unimportant whether the monocarboxylic acid is a saturated or a mono- or polyunsaturated monocarboxylic acid. The process according to the invention is preferentially suitable for saturated $C_2$-$C_8$-monocarboxylic acids and monoethylenically unsaturated $C_3$-$C_8$-monocarboxylic acids.

Saturated $C_2$-$C_8$-monocarboxylic acids are, for example, acetic acid, propionic acid, butyric acid, valeric acid (pentanoic acid), caproic acid (hexanoic acid), heptanoic acid and octanoic acid (caprylic acid), and isomers thereof. Among this group, preference is given to $C_2$-$C_8$-monocarboxylic acids such as acetic acid, propionic acid and butyric acid.

The group of the monoethylenically unsaturated monocarboxylic acids having 3 to 8 carbon atoms includes, for example, acrylic acid, methacrylic acid, dimethacrylic acid, ethacrylic acid, a-chloroacrylic acid, maleic acid, fumaric acid, itaconic acid, mesaconic acid, citraconic acid, glutaconic acid, aconitic acid, methylenemalonic acid, allylacetic acid, vinylacetic acid and crotonic acid. Preferred monoethylenically unsaturated monocarboxylic acids are acrylic acid, methacrylic acid, crotonic acid, ethacrylic acid and maleic acid.

It will be appreciated that it is also possible in the process according to the invention to use any desired mixtures of the aforementioned $C_2$-$C_{10}$-monocarboxylic acids, but preference is given to reacting only one $C_2$-$C_{10}$-monocarboxylic acid with halosilane.

The $C_2$-$C_{10}$-monocarboxylic acid used is used in equimolar amounts or in excess in relation to the halosilane. Preferably 1.0 to 2.0 mol/mol, more preferably 1.0 to 1.5 mol/mol and especially 1.0 to 1.2 mol/mol are used. An excess of $C_2$-$C_{10}$-monocarboxylic acid is required especially when the auxiliary base is contaminated by the phase-mediating extractant.

The halosilanes are those of the general formula (I)

$$SiHal_{4-x}R_x \qquad (I)$$

in which

Hal is a halogen atom selected from the group of fluorine, chlorine, bromine and iodine, R is independently hydrogen, $C_1$-$C_{10}$-alkyl or aryl and x is an integer of 0 to 3.

Preferred halogens are chlorine and bromine. When the halosilane comprises more than one halogen atom, i.e. x is unequal to 3, mixtures of the halogen atoms may also be present. However, the halosilane preferably consists only of one kind of halogen atoms, more preferably only of chlorine or bromine.

The R substituents may be the same or different and may each independently be hydrogen, $C_1$-$C_{10}$-alkyl or aryl. The R substituents are preferably the same or different and are each independently $C_1$-$C_{10}$-alkyl or aryl, and are more preferably the same and are each $C_1$-$C_4$-alkyl or phenyl.

In the context of the present invention, $C_1$-$C_{10}$-alkyl is understood to mean straight-chain or branched hydrocarbon radicals having up to 10 carbon atoms, for example methyl, ethyl, propyl, isopropyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, 2,4,4-trimethylpentyl, 1,1,3,3-tetramethylbutyl, nonyl and decyl, and isomers thereof. Preference is given to straight-chain or branched alkyl radicals having 1 to 4 carbon atoms.

In the context of the present invention, aryl is understood to mean mono- to tricyclic aromatic ring systems comprising 6 to 14 carbon ring members, for example phenyl, naphthyl and anthryl, preferably a monocyclic aromatic ring system, more preferably phenyl.

In the formula (I), x is an integer of 0 to 3, preferably an integer of 1 to 2, and, more preferably, x=1.

Typically usable halosilanes are, for example, $SiCl(CH_3)_3$, $SiCl_2(CH_3)_2$, $SiCl_3CH_3$, $SiCl(C_2H_5)_3$, $SiCl_3C_2H_5$, $SiCl(iso-C_3H_7)_3$, $SiCl(n-C_4H_9)_3$, $SiCl(tert-C_4H_9)_3$, $SiCl_3(n-C_4H_9)$, $SiCl_3(tert-C_4H_9)$, $SiCl(n-C_4H_9)(CH_3)_2$ and $SiCl(tert-C_4H_9)(CH_3)_2$, preferably $SiCl(CH_3)_3$, $SiCl(C_2H_5)_3$, $SiCl(iso-C_3H_7)_3$, $SiCl(n-C_4H_9)_3$, $SiCl(tert-C_4H_9)_3$ and $SiCl(tert-C_4H_9)(CH_3)_2$.

It will be appreciated that it is possible in the process according to the invention to use any desired mixtures of the halosilanes mentioned, but preference is given to using only one of the halosilanes mentioned.

Suitable auxiliary bases are especially those compounds which are specified as auxiliary bases in WO 03/062171 A2 and WO 05/061416 A1, Explicit reference is made here to these publications, especially to the auxiliary bases specified in WO 03/062171 A2 from page 7 line 4 to page 17 line 28, and the alkylimidazoles specified in WO 05/061416 A1, Among the auxiliary bases specified in WO 03/062171 A2, preference is given to derivatives of imidazole and of pyridine, especially 1-methylimidazole, 1-n-butylimidazole, 2-methylpyridine and 2-ethylpyridine.

According to the invention, auxiliary bases are those compounds which form a salt with the hydrogen halide formed during the reaction, said salt forming two immiscible phases with the product of value or the solution of the product of value in a suitable solvent, and being removed.

Preference is given to those auxiliary bases which are not involved in the reaction as a reactant. Additionally preferably, this auxiliary base may function as a nucleophilic catalyst in the reaction, such that the addition of a further base, for example the diethylamine or triethylamine bases cited in the literature, is not required.

Particular preference is given to those auxiliary bases which form a salt with the hydrogen halide formed during the reaction, said salt being liquid at the temperatures at which the product of value is separated from the salt.

As described above, the auxiliary base and the hydrogen halide formed during the reaction form a salt. According to the halosilane used, this is hydrogen fluoride (HF), hydrogen chloride (HCl), hydrogen bromide (BrH) or hydrogen iodide (HI), or, in the case of mixed halosilanes of the formula (I), mixtures of the hydrogen halides mentioned. In the process according to the invention, hydrogen chloride (HCl) or hydrogen bromide (HBr) is formed preferentially.

The auxiliary base is additionally suitable for removing other acids which have been added, for example, during the reaction for pH regulation, for example nitric acid, nitrous acid, carbonic acid, sulfuric acid, phosphoric acid or sulfonic acids such as methanesulfonic acid, ethanesulfonic acid, benzenesulfonic acid or p-toluenesulfonic acid.

When the reaction mixture does not comprise any further acids in addition to the $C_2$-$C_{10}$-monocarboxylic acid used, generally at least one mole of auxiliary base is used per mole of hydrogen halide to be removed, preferably 1.0 to 1.5 mol/mol, more preferably 1.0 to 1.3 mol/mol and especially 1.0 to 1.25 mol/mol. When other acids have been added, for example for pH regulation, the amount of auxiliary base has to be adjusted correspondingly.

In general, the residence time of the auxiliary base in the reaction mixture is a few minutes to several hours, preferably 5 to 120 minutes, more preferably 10 to 60 minutes and most preferably 10 to 30 minutes.

Ideally, the auxiliary base is initially charged together with the $C_2$-$C_{10}$-monocarboxylic acid to be silylated and then the halosilane is added fully or continuously.

The salt of the auxiliary base with the hydrogen halide formed during the reaction forms two immiscible phases with the product of value or a solution of the product of value in a suitable solvent. "Immiscible" means that two liquid phases separated by a phase interface form.

When the pure product of value is miscible entirely or to a relatively high degree with the salt of the auxiliary base and the hydrogen halide, a solvent can also be added to the product of value, in order to achieve demixing or a reduction in solubility. This is advisable, for example, when the solubility of the salt in the product of value or vice versa is 20% by weight or more, preferably 15% by weight or more, more preferably 10% by weight or more and most preferably 5% by weight or more. The solubility is determined under the conditions of the particular separation. The solubility is preferably determined at a temperature which is above the melting point of the salt and below, preferably 10° C. below, more preferably 20° C. below, the lowest of the following temperatures: boiling point of the product of value, boiling point of the solvent and temperature of significant decomposition of the product of value.

The solvent is considered to be suitable when the mixture of product of value and solvent is capable of dissolving the salt or the salt is capable of dissolving the product of value or a mixture of product of value and solvent to a lesser degree than the amounts specified above. Examples of usable solvents include benzene, toluene, o-, m- or p-xylene, cyclohexane, cyclopentane, pentane, hexane, heptane, octane, petroleum ether, acetone, isobutyl methyl ketone, diethyl ketone, diethyl ether, tert-butyl methyl ether, tert-butyl ethyl ether, tetrahydrofuran, dioxane, ethyl acetate, methyl acetate, dimethylformamide, dimethyl sulfoxide, acetonitrile, chloroform, dichloromethane, methylchloroform or mixtures thereof.

In general, the product of value is, however, immiscible with the salt of auxiliary base and hydrogen halide, and so the addition of a solvent can be dispensed with.

The particular advantage of the process according to the invention is that the salt of auxiliary base and hydrogen halide can be removed by a simple liquid-liquid phase separation, and so there is no need to handle solids, which is complicated in terms of process technology.

The person skilled in the art can recover the free auxiliary base in a known manner from the salt of the auxiliary base removed from the product of value, and feed it back to the process.

The free auxiliary base can be recovered, for example, by releasing the salt of the auxiliary base with a strong base, for example NaOH, KOH, $Ca(OH)_2$, milk of lime, $Na_2CO_3$, $NaHCO_3$, $K_2CO_3$ or $KHCO_3$, if appropriate in a solvent, such as water, methanol, ethanol, n- or isopropanol, n-butanol, n-pentanol or butanol or pentanol isomer mixtures or acetone. The auxiliary base thus released can, if it forms a separate phase, be removed, or, if it is miscible with the salt of the stronger base or the solution of the salt of the stronger base, be removed by distillation out of the mixture. If required, the auxiliary base released can also be removed from the salt of the stronger base or the solution of the salt of the stronger base by extraction with an extractant, such as solvents, alcohols or amines.

If required, the auxiliary base can be washed with water or aqueous NaCl or $Na_2SO_4$ solution and then dried, for example by removing any water present with the aid of an azeotropic distillation with benzene, toluene, xylene, butanol or cyclohexane.

If required, the auxiliary base can be distilled before reuse in the process according to the invention.

As described above, the auxiliary base is suitable firstly for removing the hydrogen halide formed during the reaction and secondly as a nucleophilic catalyst in the silylation of the $C_2$-$C_{10}$-monocarboxylic acid.

The performance of the silylation is not restricted and can, in accordance with the invention, be performed with scavenging of the hydrogen halide released and of any acid added, batchwise or continuously, and under air or under a protective gas atmosphere.

The silylation can be performed at ambient pressure, or else under elevated pressure or reduced pressure, preference being given to working under standard pressure.

The reaction temperature is selected such that the salt of the auxiliary base with the hydrogen halide is present in liquid form at the particular pressure, such that a liquid—liquid phase separation is possible.

Monoethylenically unsaturated $C_3$-$C_8$-monocarboxylic acids and silylation products thereof are polymerizable compounds. It is therefore important in the case of silylation of monoethylenically unsaturated $C_3$-$C_8$-monocarboxylic acids to ensure sufficient inhibition of polymerization and therefore to work in the presence of customary amounts of polymerization inhibitors known per se. Undesired polymerization is a safety hazard owing to the large amount of heat released.

In general, based on the monoethylenically unsaturated monocarboxylic acid, according to the individual substance, from 1 to 10 000 ppm, preferably from 10 to 5000 ppm, more preferably from 30 to 2500 ppm and especially from 50 to 1500 ppm of a suitable stabilizer is used.

Suitable stabilizers may, for example, be N-oxides (nitroxyl or N-oxyl radicals, i.e. compounds which have at least one >N—O·group), for example 4-hydroxy-2,2,6,6-tetramethylpiperidine N-oxyl, 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl, 4,4',4"-tris(2,2,6,6-tetramethylpiperidine N-oxyl) phosphite or 3-oxo-2,2,5,5-tetramethyl-pyrrolidine N-oxyl; mono- or polyhydric phenols which may have one or more alkyl groups, for example alkylphenols, for example o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol or 6-tert-butyl-2,4-dimethylphenol; quinones, for example hydroquinone, hydroquinone monomethyl ether, 2-methylhydroquinone or 2,5-di-tert-butylhydroquinone; hydroxyphenols, for example pyrocatechol (1,2-dihydroxybenzene) or benzoquinone; aminophenols, for example p-aminophenol; nitrosophenols, for example p-nitrosophenol; alkoxyphenols, for example 2-methoxyphenol (guaiacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol; tocopherols, for example a-tocopherol and 2,3-dihydro-2,2-dimethyl-7-hydroxybenzofuran (2,2-dimethyl-7-hydroxycoumaran), aromatic amines, for example N,N-diphenylamine or N-nitrosodiphenylamine; phenylenediamines, for example N,N'-dialkyl-p-phenylenediamine, where the alkyl radicals may be the same or different and each consist independently of from 1 to 4 carbon atoms and may be straight-chain or branched, for example N,N'-dimethyl-p-phenylenediamine or N,N'-diethyl-p-phenylenediamine, hydroxylamines, for example N,N-diethylhydroxylamine, imines, for example methyl ethyl imine or methylene violet, sulfonamides, for example N-methyl-4-toluenesulfonamide or N-tert-butyl-4-toluenesulfonamide, oximes, such as aldoximes, ketoximes or amide oximes, for example diethyl ketoxime, methyl ethyl ketoxime or salicylaldoxime, phosphorus compounds, for example triphenylphosphine, triphenyl phosphite, triethyl phosphite, hypophosphorous acid or alkyl esters of phosphorous acids; sulfur compounds, for example diphenyl sulfide or phenothiazine; metal salts such as copper or manganese, cerium, nickel, chromium salts, for example chlorides, sulfates, salicylates, tosylates, acrylates or acetates, for example copper acetate, copper(II) chloride, copper salicylate, cerium (III) acetate or cerium(III) ethylhexanoate, or mixtures thereof.

The polymerization inhibitor (mixture) used is preferably at least one compound from the group of hydroquinone, hydroquinone monomethyl ether, phenothiazine, 4-hydroxy-2,2,6,6-tetramethylpiperidine N-oxyl, 4-oxo-2,2,6,6-tetramethylpiperidine N-oxyl, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol, 2-methyl-4-tert-butylphenol, hypophosphorous acid, copper acetate, copper(II) chloride, copper salicylate and cerium(III) acetate.

Very particular preference is given to using phenothiazine and/or hydroquinone monomethyl ether (MEHQ) as the polymerization inhibitor.

Preference is given to using the polymerization inhibitor (mixture) in the form of an aqueous solution.

To further support the stabilization, an oxygenous gas may be present, preferably air or a mixture of air and nitrogen (lean air).

The silylation reactants and any other assistants present, such as solvents or polymerization inhibitors, can be added as desired.

In a preferred embodiment, the $C_2$-$C_{10}$-monocarboxylic acid and the auxiliary base are each initially charged at least partly, preferably each fully, in a suitable reactor and heated. Subsequently, the halosilane is metered in, the metered addition generally being effected within a few minutes to several hours, preferably 5 to 120 minutes, more preferably 10 to 60 minutes and most preferably 10 to 30 minutes, continuously or in portions.

The silylation is followed, as described, by the liquid-liquid removal of the salt of the auxiliary base and the subsequent recovery of the auxiliary base from the phase removed.

The silylated $C_2$-$C_{10}$-monocarboxylic acids prepared by the process according to the invention can be used as comonomers in copolymers for a wide variety of different uses.

The examples which follow are intended to illustrate the invention, but without restricting it.

Percentage and ppm data used in this document are based, unless stated otherwise, on percentages and ppm by weight.

EXAMPLES

Example 1

Preparation of Trimethylsilyl Methacrylate

A 1 l reaction vessel was initially charged, with exclusion of moisture, with 220.5 g (2.54 mol) of methacrylic acid which had been stabilized with 250 ppm of hydroquinone monomethyl ether. 231.3 g (2.81 mol) of 1-methylimidazole were rapidly added dropwise, and the addition proceeded slightly exothermically. At 80° C., 281.1 g (2.59 mol) of chlorotrimethylsilane were added dropwise within 20 minutes. After about one third of the metered addition, the reaction mixture became cloudy, and a second phase formed. On completion of the metered addition, the lower phase was allowed to settle out at 90° C., and 330 g of the lower phase were removed.

408 g of trimethylsilyl methacrylate (99% yield) were obtained in the upper phase in a purity of 98% (GC analysis), which had been admixed with 25 ppm of phenothiazine.

Comparative Example 1

Preparation of Trimethylsilyl Methacrylate

A 0.5 l reaction vessel was initially charged, with exclusion of moisture, with 50.0 g (0.58 mol) of methacrylic acid which had been stabilized with 250 ppm of hydroquinone monomethyl ether in 250 ml of toluene with stirring. 58.8 g (0.58 mol) of triethylamine were rapidly added dropwise, and the addition proceeded slightly exothermically. At 50° C., 63.7 g (0.59 mol) of chlorotrimethylsilane were added dropwise within 20 minutes. A thick white suspension formed rapidly, and the mixture was now stirrable only with difficulty. The suspension was filtered off with suction through a glass suction filter and the filtercake was washed twice with toluene.

After the solvent had been removed on a rotary evaporator, 63.4 g of trimethylsilyl methacrylate (58% yield) were obtained in a purity of 84% (GC analysis).

Example 2

Preparation of Trimethylsilyl Methacrylate

A 1 m³ steel/enamel stirred tank was initially charged, with exclusion of moisture and oxygen, with 289 kg (3.51 kmol) of 1-methylimidazole. Subsequently, 363 kg of pure methacrylic acid (4.21 kmol; 1.2 equivalents) were metered in within one hour, in the course of which the internal temperature rose to 45° C. Then 381 kg (3.51 kmol) of chlorotrimethylsilane were added within two hours, in the course of which a temperature rise to 84° C. was observed. Subsequently, stirring was continued at a temperature of 90° C. for 45 minutes and the phase separation was carried out. 476 kg of 1-methylimidazolium chloride lower phase and 557 kg of upper phase were obtained, which consisted to an extent of 99% (GC analysis) of the trimethylsilyl methacrylate product (yield: 99%). The product was stabilized with 250 ppm of phenothiazine.

Example 3

Preparation of Trimethylsilyl Acetate

In a 2 l reaction vessel, 403 g (6.70 mol) of acetic acid were mixed with 550 g (6.70 mol) of 1-methylimidazole and then admixed slowly with 728 g (6.70 mol) of chlorotrimethylsilane. After the addition had ended, the reaction mixture was heated to 90° C. and stirred for one hour, and the phase separation was performed within two hours. 804 g of 1-methylimidazolium chloride lower phase and 867 g of product upper phase were obtained. The upper phase consisted to an extent of 97% (GC analysis) of trimethylsilyl acetate, which corresponds to a yield of 95%.

Example 4

Preparation of Trimethylsilyl Acrylate

A 2 l reaction vessel was initially charged with 517 g of 1-methylimidazole (6.30 mol) and 684.3 g (6.30 mol) of chlorotrimethylsilane were metered in slowly, in the course of which the internal temperature rose to 50° C. Subsequently, 454 g of acrylic acid (6.30 mol) were added, in the course of which the temperature of the reaction mixture rose to 70° C. After the addition had ended, the mixture was stirred at 85° C. for one hour and the phase separation was awaited over the course of two hours. 783 g of 1-methylimidazolium chloride lower phase and 859 g of product upper phase were obtained. The latter consisted to an extent of 96% (GC analysis) of trimethylsilyl acrylate, which corresponds to a yield of 90%.

Example 5

Preparation of Dimethylsilyl Bismethacrylate

A 2 l reaction vessel was initially charged with 550 g of 1-methylimidazole (6.70 mol) and 697 g (8.10 mol; 1.2 equivalents) of methacrylic acid were metered in slowly, in the course of which the internal temperature rose to 60° C. Subsequently, 437 g of dichlorodimethylsilane (3.37 mol) were added; the temperature of the reaction mixture was kept at 60° C. by external cooling. After the addition had ended, the mixture was stirred at 85° C. for one hour and the phase separation was awaited over the course of two hours. 903 g of 1-methylimidazolium chloride lower phase and 765 g of product upper phase were obtained. The latter consisted to an extent of 98% (GC analysis) of dimethylsilyl bismethacrylate, which corresponds to a yield of 97%.

The invention claimed is:

1. A process for preparing a silylated monocarboxylic acid by reacting a $C_2$-$C_{10}$-monocarboxylic acid with a halosilane of the general formula (I)

$$SiHal_{4-x}R_x \quad (I)$$

in which
Hal is a halogen atom selected from the group consisting of fluorine, chlorine, bromine and iodine,
R is independently hydrogen, $C_1$-$C_{10}$-alkyl or aryl and
x is an integer of 0 to 3
to form a hydrogen halide in the presence of an auxiliary base, wherein the auxiliary base and the hydrogen halide form a salt, which is liquid at the temperatures at which the product of value is separated from the salt, and which forms two immiscible phases with the product of value or the solution of the product of value in a suitable solvent and is removed, wherein the auxiliary base is selected from the group consisting of 1-methylimidazole, 1-n-butylimidazole, 2-methylpyridine and 2-ethylpyridine.

2. The process according to claim 1, wherein the $C_2$-$C_{10}$-monocarboxylic acid is selected from the group consisting of a saturated $C_2$-$C_8$-monocarboxylic acid and a monoethylenically unsaturated $C_3$-$C_8$-monocarboxylic acid.

3. The process according to claim 2, wherein the saturated $C_2$-$C_8$-monocarboxylic acid is selected from the group consisting of acetic acid, propionic acid and butyric acid.

4. The process according to claim 2, wherein the monoethylenically unsaturated $C_2$-$C_8$-monocarboxylic acid is selected from the group consisting of acrylic acid, methacrylic acid, crotonic acid, ethacrylic acid and maleic acid.

5. The process according to claim 1, wherein the halogen atom of the halosilane is chlorine or bromine.

6. The process according to claim 1, wherein the R substituents of the halosilane are the same and are each $C_1$-$C_4$-alkyl or phenyl.

7. The process according to claim 1, wherein the halosilane is selected from the group consisting of $SiCl(CH_3)_3$, $SiCl_2(CH_3)_2$, $SiCl_3CH_3$, $SiCl(C_2H_5)_3$, $SiCl_3C_2H_5$, $SiCl(iso-C_3H_7)_3$, $SiCl(n-C_4H_9)_3$, $SiCl(tert-C_4H_9)_3$, $SiCl_3(n-C_4H_9)$, $SiCl_3(tert-C_4H_9)$, $SiCl(n-C_4H_9)(CH_3)_2$ and $SiCl(tert-C_4H_9)(CH_3)_2$.

8. The process according claim 1, wherein the auxiliary base simultaneously functions as a nucleophilic catalyst for the silylation.

9. The process according to claim 1, wherein at least one mole of auxiliary base is used per mole of hydrogen halide to be removed.

10. The process according to claim 9, wherein the salt of the auxiliary base has a solubility in the product of value or in the solution of the product of value in a suitable solvent of less than 20% by weight.

11. The process according to claim 1, wherein the $C_2$-$C_{10}$-monocarboxylic acid and the auxiliary base are at least partly initially charged in a reactor and then the halosilane is metered in.

12. The process according to claim 1, wherein the auxiliary base is present in the reaction for a time of from 5 to 120 minutes.

13. The process according to claim 1, wherein the auxiliary base is present in the reaction for a time of from 10 to 30 minutes.

14. The process according to claim 1, wherein the suitable solvent is at least one selected from the group consisting of benzene, toluene, o-xylene m-xylene, p-xylene, cyclohexane, cyclopentane, pentane, hexane, heptane, octane, petroleum ether, acetone, isobutyl methyl ketone, diethyl ketone, diethyl ether, tert-butyl methyl ether, tert-butyl ethyl ether, tetrahydrofuran, dioxane, ethyl acetate, methyl acetate, dimethylformamide, dimethyl sulfoxide, acetonitrile, chloroform, dichloromethane and methylchloroform.

15. The process according to claim 1, wherein the reaction is conducted under standard pressure.

16. The process according to claim 1, wherein the reaction is conducted in the presence of a stabilizer.

17. The process according to claim 16, wherein the stabilizer is present in an amount of from 1 to 10 000 ppm based on the monoethylenically unsaturated monocarboxylic acid.

18. The process according to claim 1, wherein the reaction is conducted in the presence of an oxygenous gas.

* * * * *